United States Patent

Draenert et al.

[11] Patent Number: 6,083,263
[45] Date of Patent: *Jul. 4, 2000

[54] ADJUSTABLE HIP-JOINT ENDOPROSTHESIS

[76] Inventors: Klaus Draenert, Gabriel-Max-Str 3, D-8000 München 90; Ortwin Piper, Hermann-Essig-Strasse 26, D7141, Schwieberdingen, both of Germany

[*] Notice: This patent is subject to a terminal disclaimer.

[21] Appl. No.: 08/833,688

[22] Filed: Apr. 8, 1997

Related U.S. Application Data

[62] Continuation of application No. 08/675,371, Jul. 2, 1996, abandoned, which is a continuation of application No. 08/199,200, filed as application No. PCT/EP92/01925, Aug. 21, 1992, abandoned.

[30] Foreign Application Priority Data

Aug. 23, 1991 [DE] Germany ............................. 41 27 989
Jan. 14, 1992 [DE] Germany ............................. 42 00 749

[51] Int. Cl.$^7$ ........................................................ A61F 2/36
[52] U.S. Cl. ................................................................ 623/23
[58] Field of Search ............................. 623/18, 22, 23; 903/103, 104, 350, 385

[56] References Cited

U.S. PATENT DOCUMENTS 4,051,559  10/1977  Pifferi ........................................ 623/22
5,002,581  3/1991   Paxson ...................................... 623/23
5,336,268  8/1994   Rispeter .................................... 623/23

FOREIGN PATENT DOCUMENTS 0 339 530      11/1989  European Pat. Off. .
0 393 608 A3   10/1990  European Pat. Off. .
2 575 383       7/1986  France .
2 578 738       9/1986  France .
2 605 514       4/1988  France .
WO 90/02533     3/1990  Germany .
9002533         3/1990  WIPO ..................................... 623/23

*Primary Examiner*—Michael J. Milano
*Attorney, Agent, or Firm*—Kinney & Lange, P.A.

[57] ABSTRACT

A hip-joint endoprosthesis is provided which has a prosthesis head (5) that can be medio-laterally displaced parallel to a tangent that rests on the lateral edge of the proximal femoral infundibulum of the hip-joint (b) and contacts the inner contour of the curved neck of the femur (b'). This hip-joint endoprosthesis allows the centre of rotation of the hip-joint to be reproducibly adjusted by means of an adjustable head (5). Toothings (12, 13, 15, 16) ensure a (fine) stepped adjustability of the displacement in the medio-lateral direction (B—B') and of the rotation around an axis (A—A) that is perpendicular to the plane of displacement (B—B'). Securing is allowed by a single screw (10) that braces the engaged toothings (12, 13, 15, 16) against each other. The height of the joint ball (6) mounted on the prosthesis head (5) via a cone (17) can be adjusted by joint balls (6) having pressed-in cones of varying depths.

18 Claims, 3 Drawing Sheets

ADJUSTABLE HIP-JOINT ENDOPROSTHESIS

This is a continuation of application Ser. No. 08/675,371, filed Jul. 2, 1996 now abandoned, which is a continuation of Ser. No. 08/199,200, filed Jun. 09, 1994 now abandoned which is a 371 06 PCT/EP92/01925, filed Aug. 21, 1992.

The invention relates to a hip-joint endoprosthesis.

Although for orthopaedic surgeons the artificial replacement of a hip-joint has become an operation which is one of the most frequent surgical interventions, nevertheless many problems associated with the artificial replacement of joint components have not yet been solved to date.

On account of the great variety of morphological variants of the femur and the pelvis there is hardly an appreciable correlation between individual parameters despite the physiological interaction of muscular forces and lever arms of the supporting structure (PC Noble, Proximal femoral geometry and the design of cementless hip replacements, Orthop Rel Sci 1, 86–92). A number of problems ensue from this which have been solved only incompletely so far; for instance, the length of the neck of the femur could so far only roughly be imitated by means of three neck components which are different in size. The adjustment of the centre of the head was dependent on the choice of the angle between femoral neck and shaft (femoral neck/shaft angle), which has lately been increasingly chosen to be valgus, i.e. at about 140°, in contrast to about 126 to 130° of the physiological angle. Thereby it was intended to achieve a lower bending and shearing stress on the femoral bed. However, the lateralization of the resultant force reflected from the ground lead to a fast detrition of the pans.

It is known from the cementless prostheses that with an optimum adaptation to the bone a uniform transmission of forces may be expected (Walker P, Poss R, Robertson D D, Reilly D T, Ewald F C, Thomas W H and Sledge C B, Design analysis of press-fit hip stems, Orthop Rel Sci 1, 75–85). From the decision for an optimum adaptation to the bony bed, however, ensues the problem of variably adjusting and permanently fixing the height and the projection of the centre of the head. In this connection, the stability of the articulate junction involves particular difficulties.

FR-A1-2 605 514 discloses a hip-joint prosthesis in which the prosthesis head can be adjusted in three directions. For this purpose, the prosthesis consists of three parts. The prosthesis head is mounted on a peg fixed in the femur and bears a joint ball on a cone. The distance between the centre of the joint ball and the centre line of the prosthesis is adjusted by means of joint balls having more or less deeply pressed-in cones. The height of the centre of the joint ball along the centre line of the prosthesis can be adjusted by means of prosthesis heads having different overall heights. For a rotation around the centre axis of the prosthesis, the prosthesis head is supported in a peg protruding from a prosthesis shaft; the rotation is fixed by a screw bracing the prosthesis head against the prosthesis shaft.

Furthermore, EP-A1-0 390 883 discloses a hip-joint prosthesis being provided with a head part which is placed on a neck part connected with a peg and can be arranged in a one-, two- or three-dimensionally adjustable manner. A displacement in a frontal and/or sagittal plane is provided by two rails perpendicular to each other, for instance in dovetail guides. It is also suggested that tilting in the sagittal plane and adjustment in the vertical direction be also provided. The adjustments are to be fixed by screws.

It is an object of this invention to provide an improved adjustable hip-joint endoprosthesis which is adaptable to the patient's orthopaedic conditions during the operation, allows a uniform transmission of forces, and ensures a stable fixing of the adjustments.

This object is achieved according to the invention by the features of the claims. The hip-joint endoprosthesis of the invention allows an adjustment of the prosthesis head in the horizontal plane, without a step being formed, along a tangent of Shenton's line in the medial end portion. According to the invention, the direction of the plane of the medio-lateral displacement is adjusted such that it is aligned parallel to a tangent starting from the lateral edge of the proximal metaphysial infundibulum and contacting the medial inner limitation of the neck of the femur.

The invention advantageously provides a hip-joint endoprosthesis which is to a great extent adjustable without an exchange of individual elements. The prosthesis is adapted to the patient's orthopaedic conditions by adjusting the prosthesis head during the operation. For this purpose, stepwise adjustments are possible both in the medio-lateral direction and in the torsion angle of the prosthesis by means of rotation around the axis of the femoral shaft. These adjustments are preferably fixed by positive locking via toothings. An alteration of these adjustments by external forces without removing the positive locking is only possible if these forces lead to the fracture of the prosthesis.

These toothings furthermore allow the separate adjustment of the prosthesis in both directions of movement with small forces without a need of changing the respectively other adjustment. For simultaneously fixing both adjustments, only one fastening element, e.g. a threaded bolt, an expanding bolt or body-bound rivet which can be driven in, or the like is necessary.

Joint balls having inner cones which differ in their depths are intended to be used for the adjustment in the proximal-distal direction, wherein the joint balls may be different in size.

All adjustment and fixing means are designed and arranged in such a way that they are readily accessible to the operating surgeon.

An embodiment of the invention is represented in the drawing and will be described in more detail in the following.

Figure 1:
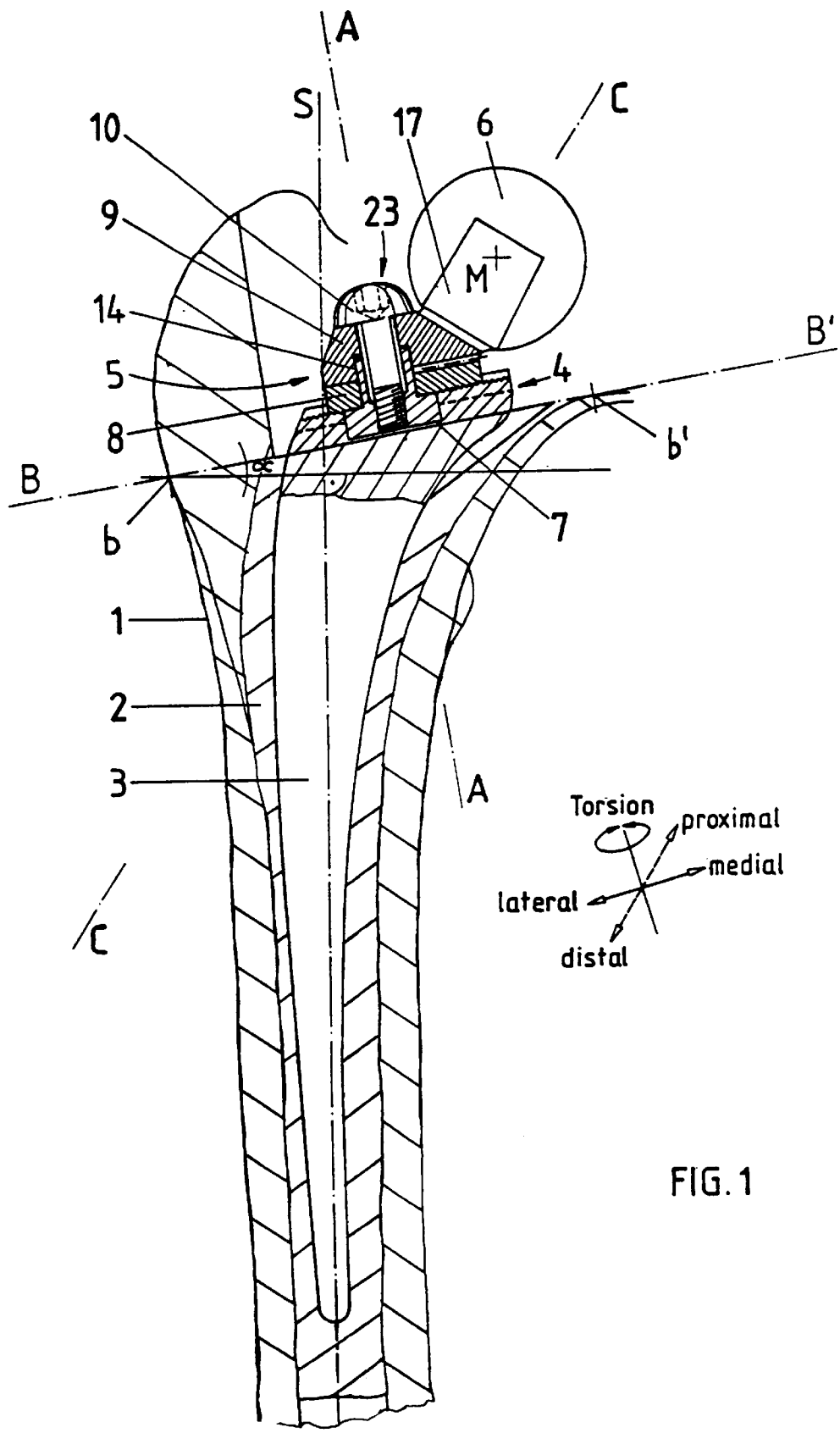
FIG. 1 shows a femur with an adjustable hip-joint endoprosthesis according to the invention.
Figure 2:
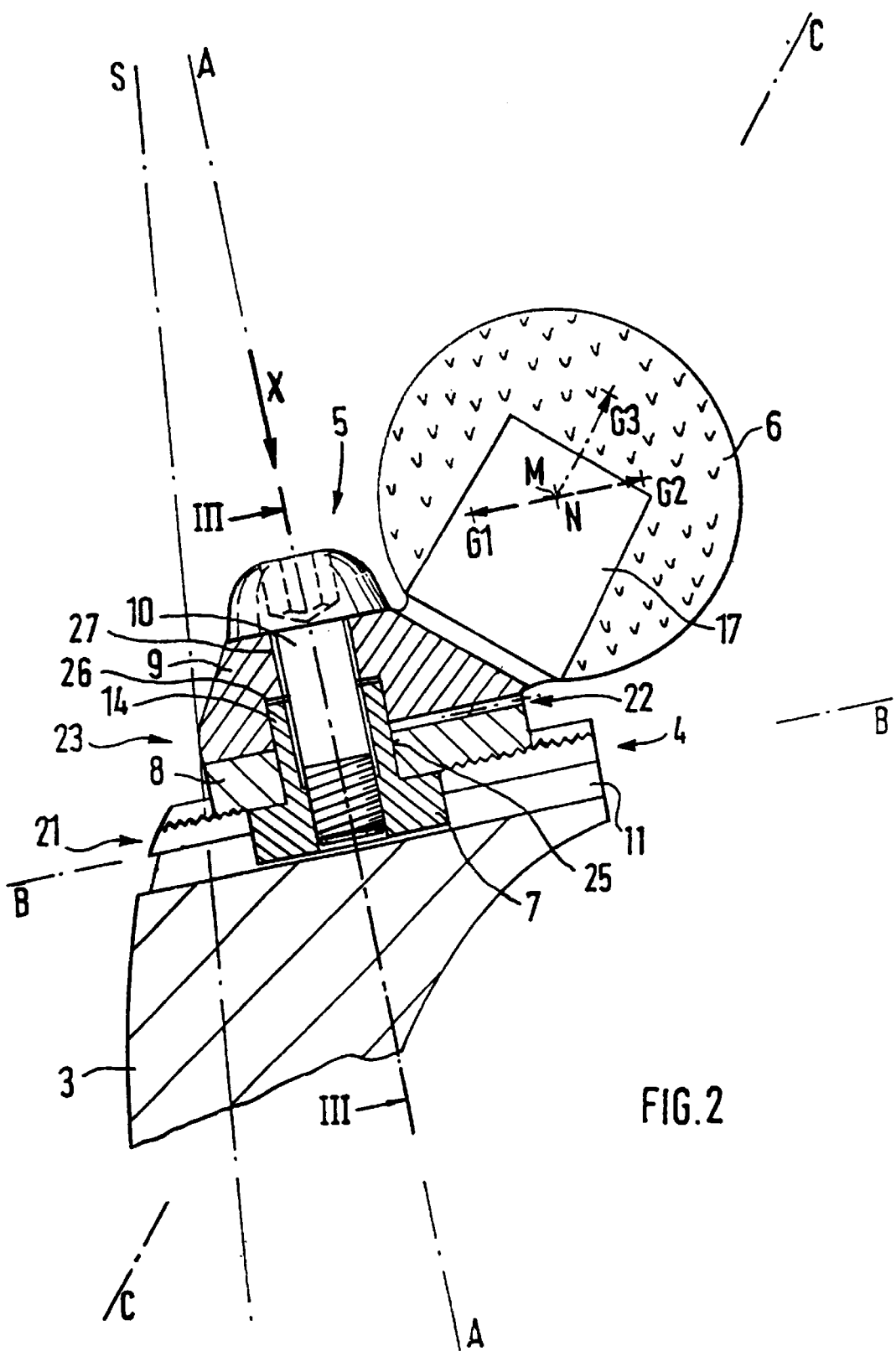
FIG. 2 shows a section through a hip-joint endoprosthesis in a frontal plane.

FIG. 1 shows a femur 1 with a hip-joint endoprosthesis surrounded by a bone cement sheath 2. The endoprosthesis consists of a shaft or stem 3, a connecting element or groove element 4 incorporated therein, and a prosthesis head 5 which is movable relative to the groove element 4, which head bears a joint ball 6 and comprises a setting element or adjustment element 7, an intermediate plate 8 and a supporting member 9 with a fastening element which may be a threaded bolt 10. Locking means 21, 22 formed by front toothings 12, 13 and 15, 16 are arranged between the supporting member 9 and the intermediate plate 8 on the one hand, and between the groove element 4 and the intermediate plate 8 on the other hand (FIG. 2). The adjustment means allowing the adaptation of the endoprosthesis to the orthopaedic circumstances is as a whole designated by the reference sign 23 in the Figures. The hip-joint endoprosthesis is inserted along a shaft axis S into the femur 1 and fixed there in the bone cement sheath 2. All edges of the hip-joint endoprosthesis and the adjustment means 23 including the groove element 4 are rounded as far as possible, in particular in the medio-proximal end portion of the prosthesis, in order to avoid stress concentrations by which the bone cement sheath 2 could be damaged or destroyed.

At least three adjustment directions are provided for the adjustment of an orthopaedically correct position of the joint ball 6. A first adjustment is carried out by a linear displacement in the medio-lateral direction according to a line B–B', a second adjustment is carried out in the proximal-distal direction according to a line C—C and a third adjustment is carried out by the rotation around an axis A—A, which, seen onto a frontal plane according to FIG. 1, is perpendicular to the line B–B'.

Figure 3:
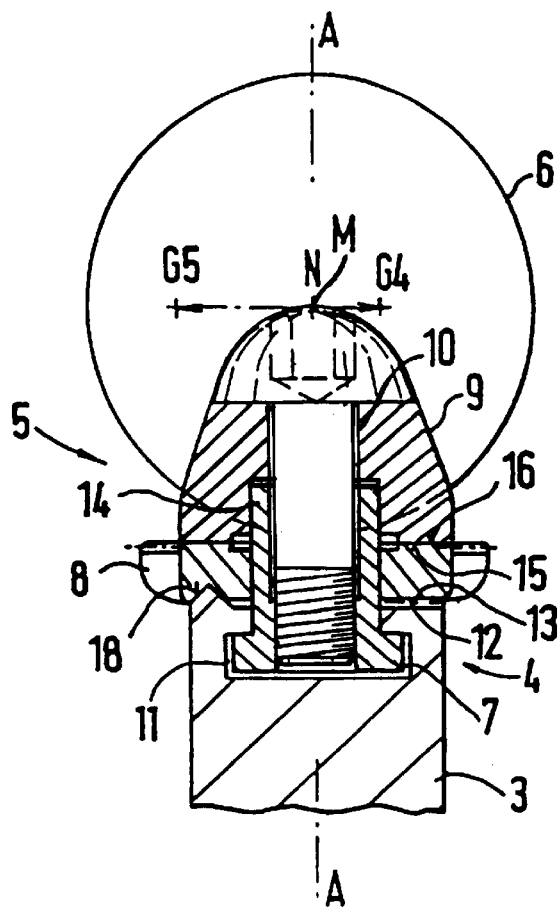
FIG. 3 shows a section according to the line III—III in FIG. 2.

In FIG. 2, a sectional view of the groove element 4 is shown, which has an undercut groove 11 in the medio-lateral direction at its surface facing the head part, in which groove the adjustment element 7 is guided. Due to the undercut, the adjustment element 7 can only be moved linearly in the direction of the groove 11. The first linear front toothing 12 is arranged on the surface of the groove element 4. Above the groove element 4, the intermediate plate 8 is supported on whose surface facing the groove element 4 the second linear front toothing 13 is arranged, which forms the counterpart to the first linear front toothing 12 and engages with it. The front toothing 12 extends along the entire length of the groove element 4 and is only arranged on one side opposite to a prismatic guide 18 (FIG. 3). FIG. 2 shows the proximal end of the prosthesis shaft 3 and the groove element 4 only schematically for explaining the adjustability of the prosthesis head 5. As explained above, the edges of the groove element 4 and the prosthesis shaft 3—as shown in FIG. 1—are preferably also rounded in the proximal shaft area in order to avoid strain and stress concentrations, which could destroy the bone cement sheath 2.

A bore 25 in the intermediate plate 8 receives a peg 14 of the adjustment element 7. The first radial front toothing 15 of the locking means 22 is arranged in a raised manner radially to the centre of said bore 25 and opposite to the second linear front toothing 13 on the upper side of the intermediate plate 8, said first radial front toothing 15 being limited by an area having approximately the shape of a segment of a circle. The intermediate plate 8 can laterally extend beyond the groove element 4 in the area of the radial front toothing 15.

The supporting member 9 rests on the intermediate plate 8 and the peg 14 of the adjustment element 7 extends into a blind bore 26 of the supporting member 9. As an elongation of said bore 26, a bore 27 with a smaller diameter is provided through which the threaded bolt 10 is screwed through the supporting element 9 into an internal thread in the peg 14 of the adjustment element 7. The supporting member 9 bears the second radial front toothing 16 opposite and corresponding to the first radial front toothing 15. The area limiting said second radial front toothing 16 and having the shape of a segment of a circle encloses a smaller angle than the area limiting said first radial front toothing 15.

The supporting member 9 is provided with a shaft bearing an outer cone 17 at its end. The joint ball 6 into which a corresponding inner cone is worked in is mounted on said cone, wherein the extent to which the cone 17 enters the ball joint 6 is called press-in depth. The adjustment in the proximal-distal direction according to the line C—C is performed by ball joints 6 having inner cones with different depths.

FIG. 3 shows a section of the groove element 4 with the prismatic guide 18 arranged on one side as well as the groove 11. Both guides are incorporated at the head-side of stem 3.

In FIG. 1, a neutral or initial position of the centre of the joint ball 6 is designated by M. The centre of said joint ball 6 can be displaced from said position parallel to the line B–B' into the centre of rotation of the hip-joint as intended end position.

Figure 4:
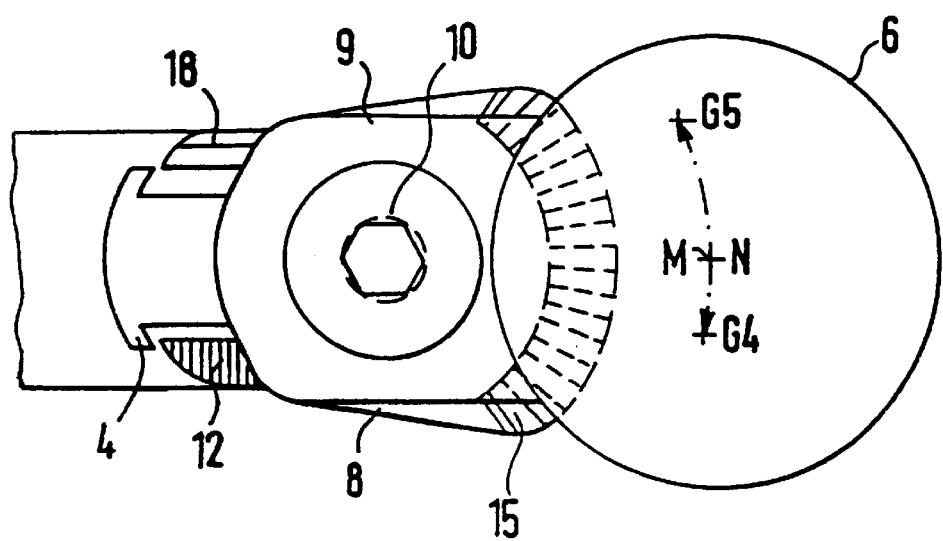
FIG. 4 shows a top view seen in the direction of the arrow X in FIG. 2.

In FIGS. 2 to 4, a neutral position of the centre M of the joint ball 6 is designated by N, corresponding to an initial position. The centre of the joint ball 6 can be linearly displaced from the neutral position N in the direction B–B' within the limits G1 and G2 (FIG. 2). The centre of the joint ball 6 can be step-wise adjusted up to a limit G3 in the direction of the line C—C by using joint balls 6 with inner cones having different depths (FIG. 2). Finally, a displacement on an arc of a circle around the axis A—A within the limits G4 and G5 is possible (FIG. 4).

For the construction of the medio-lateral displacement plane, an angle $\alpha$ is defined between a line perpendicular to the shaft axis S and the line B–B'. The line B–B' laterally (point b) rests on or intersects the infundibulum edge of the proximal femoral metaphysis. The point b is the projection of the lateral infundibulum edge in an X-ray image in the sagittal path of the rays a–p (anterior-posterior). On the medial side the line B–B' contacts the arc-shaped inner limitation of the curved neck of the femur at point b'. The angle $\alpha$ ranges between 1 and 15°, preferably between 2 and 10°, more preferably between 2 and 4°. On account of the chosen angle $\alpha$, the displacement of the prosthesis head along the line B–B' allows a uniform transmission of forces, since, a displacement of the prosthesis head 5 by means of the adjustment means follows Shenton's line without steps.

The hip-joint endoprosthesis is adjusted in that the prosthesis head 5 is displaced in the medio-lateral direction parallel to a tangent which rests on the lateral edge of the proximal femoral infundibulum of the hip joint and contacts the inner contour of the curved neck of the femur. The adjustment is preferably performed after having inserted the shaft 3 into the femur. However, the method of adjusting the hip-joint endoprosthesis can also be performed outside the body by means of an X-ray image and all necessary adjustments can be made there. It is also possible that the hip-joint endoprosthesis is already previously adjusted in a laboratory on the basis of X-ray images and independent of performing the surgical operation.

In the preferred method, the adjustment element 7 is pushed into the groove 11 after inserting the shaft 3 with the groove element 4 into the femur 1. The intermediate plate 8 and the supporting member 9 are placed onto the groove element 4 such that the peg 14 of the adjustment element 7 penetrates through the bore 25 of the intermediate plate 8 into the blind hole 26 of the supporting member 9. The arrangement is initially fixed by tightening the threaded bolt 10 such that the individual parts are only just displaceable against each other across the toothings 12, 13 and 15, 16.

A joint ball 6 chosen previously according to the press-in depth of the inner cone and the ball size is mounted on the cone 17 of the supporting member 9. The press-in depth of the cone determines the distance between the centre M of the joint ball 6 and the surface of the groove element 4. Subsequently, the distance of the centre of the joint ball 6 from the shaft axis S is adjusted by displacing the prosthesis head 5 in the groove 11 along the direction B–B'. After rotating the supporting member 9 around the peg 14 of the adjustment element 7, the adjustments are fixed by tightening the threaded bolt 10. Thereby the paired toothings 12, 13 and 15, 16 are braced against each other and transmit the forces acting on the joint ball 6 to the groove element 4 and thus the shaft 3 by positive locking.

Forces whose directions do not run through the axis A—A try to rotate the prosthesis head 5 around said axis A—A. These forces are transmitted from the supporting member 9 to the intermediate plate 8 via the second pair of toothings 15, 16 and from said intermediate plate 8 to the groove element 4 by means of the prismatic guide 18. Other forces are transmitted from the supporting member 9 to the intermediate plate 8 via the peg 14 and from there to the groove element 4 via the prismatic guide 18 or the first pair of toothings 12, 13, depending on their direction.

We claim:

1. A hip-joint endoprosthesis for implantation in a femur, said femur having on a lateral side thereof a proximal femoral infundibulum with a lateral edge, and on a medial side thereof a curved neck with an inner contour, said hip-joint endoprosthesis comprising:

a shaft having an axis; and an adjustable prosthesis head displaceable relative to the shaft in a medio-lateral direction within a plane, said plane of the medio-lateral displaceability of the prosthesis head being parallel to a tangent that rests on the lateral edge of the proximal femoral infundibulum and contacts the inner contour of the curved neck of the femur, wherein the plane of the medio-lateral displaceability is inclined in a medially ascending manner by an angle $\alpha$, which is between 1 and 15°, relative to a line which is perpendicular to the shaft axis of the prosthesis.

2. A hip-joint endoprosthesis for implantation in a femur, said femur having on a lateral side thereof a proximal femoral infundibulum with a lateral edge, and on a medial side thereof a curved neck with an inner contour, said hip-joint endoprosthesis comprising:

a shaft having an axis; and an adjustable prosthesis head displaceable relative to the shaft in a medio-lateral direction within a plane, said plane of the medio-lateral displaceability of the prosthesis head being parallel to a tangent that rests on the lateral edge of the proximal femoral infundibulum and contacts the inner contour of the curved neck of the femur, wherein the prosthesis head comprises:

a stationary groove element mounted to the shaft in the plane of the medio-lateral displaceability;

a joint ball;

a supporting member for supporting the joint ball on the stationary groove element;

an adjustment means for adjusting the prosthesis head relative to the shaft, the adjustment means comprising an adjustment element which is guided in the stationary groove element and an intermediate plate for displaceably supporting the adjustment element relative to the groove element;

locking means for fixing the adjustment means to the shaft; and at least one fastening element extending through said adjustment means for interlocking the locking means with each other.

3. The hip-joint endoprosthesis according to claim 2, wherein the adjustment element comprises a cylindrical peg with which the intermediate plate is connected in a linearly displaceable manner and on which the supporting member is pivotably supported.

4. The hip-joint endoprosthesis according to claim 2, wherein the locking means consist of opposite toothings, wherein a first pair of toothings is arranged between the supporting member and the intermediate plate and a second pair of toothings is arranged between the groove element and the intermediate plate.

5. The hip-joint endoprosthesis according to claim 4, wherein the first pair of toothings consists of a linear front toothing which is arranged on at least one front surface of the groove element and is engaged with a corresponding opposite toothing at the intermediate plate.

6. The hip-joint endoprosthesis according to claim 4, wherein the second pair of toothings consist of a radial front toothing on a surface of the supporting member which is engaged with a corresponding opposite toothing at the intermediate plate.

7. The hip-joint endoprosthesis according to claim 2, wherein the prosthesis head further comprises a one-sided prismatic guide for guiding the intermediate plate on the groove element.

8. The hip-joint endoprosthesis according to claim 7, wherein the adjustment element is linearly displaceable on the prismatic guide of the groove element in the direction of the plane of the medio-lateral displaceability.

9. The hip-joint endoprosthesis according to claim 8, wherein the groove element and the prismatic guide are worked in at the head of the shaft.

10. A hip-joint endoprosthesis for implantation in a femur, said femur having on a lateral side thereof a proximal femoral infundibulum with a lateral edge, and on a medial side thereof a curved neck with an inner contour, said hip-joint endoprosthesis comprising:

a shaft having an axis, the shaft being fixable to the femur;

an adjustable prosthesis head connected to the shaft, the prosthesis head comprising:

a stationary groove element mounted to the shaft;

a joint ball;

a supporting member for supporting the joint ball on the stationary groove element;

an adjustment means for adjusting the prosthesis head relative to the shaft, the adjustment means comprising an adjustment element which is guided in the stationary groove element and an intermediate plate for displaceably supporting the adjustment element relative to the groove element;

locking means for fixing the adjustment means to the shaft; and at least one fastening element extending through said adjustment means for fixing the locking means in position.

11. The hip-joint endoprosthesis according to claim 10, wherein the intermediate plate is guided on the groove element via a one-sided prismatic guide.

12. The hip-joint endoprosthesis according to claim 11, wherein the adjustment element is linearly displaceable on the prismatic guide of the groove element in the direction of the plane.

13. The hip-joint endoprosthesis according to claim 12, wherein the groove element and the prismatic guide are worked in at the head of the shaft.

14. A method for adjusting a hip-joint endoprosthesis used for implantation in a femur, said femur having on a lateral side thereof a proximal femoral infundibulum with a lateral edge, and on a medial side thereof a curved neck with an inner contour, said hip-joint endoprosthesis comprising a shaft and an adjustable prosthesis head, said method comprising the steps of:

displacing the prosthesis head relative to the shaft in a medio-lateral direction parallel to a tangent that rests on the lateral edge of the proximal femoral infundibulum and contacts the inner contour of the curved neck of the femur.

15. A method for adjusting a hip-joint endoprosthesis used for implantation in a femur, said femur having on a lateral side thereof a proximal femoral infundibulum with a lateral edge, and on a medial side thereof a curved neck with an inner contour, said hip-joint endoprosthesis comprising a shaft fixable to the femur and an adjustable prosthesis head connected to the shaft, the adjustable prosthesis head having a groove element extending in a plane of a medio-lateral displaceability of the prosthesis head, a joint ball, a support member for supporting the joint ball on the groove element, and a locking mechanism for locking the prosthesis head to the shaft, said method comprising the steps of:

displacing the prosthesis head in the groove element in the plane of medio-lateral displaceability to provide a displacement adjustment; rotating the prosthesis head around an axis which is perpendicular to said plane of medio-lateral displaceability to provide a rotating adjustment;

fixing both the displacement and the rotating adjustments via locking means.

16. The method for adjusting a hip-joint endoprosthesis according to claim 15, further comprising the step of adjusting the prosthesis head in a proximal-distal direction which lies between the plane of medio-lateral displaceability and the axis, such that the joint ball is chosen from a group of joint balls having different press-in depths, wherein the distance of the joint ball from a surface of the groove element is determined by the press-in depth.

17. An adjustable prosthesis head for a hip-joint endoprosthesis for implantation in a femur, said femur having on a lateral side thereof a proximal femoral infundibulum with a lateral edge, and on a medial side thereof a curved neck with an inner contour, the adjustable prosthesis head comprising:

a groove element comprising an undercut groove extending in a plane of a medio-lateral displaceability of the prosthesis head, and a first linear front toothing provided on one surface of the groove element perpendicular to said undercut groove;

an adjustment element guided in said undercut groove and including a cylindrical peg which includes a bore with an internal thread;

an intermediate plate resting on said groove element, the intermediate plate having a bore which receives the peg, and a second linear front toothing for engaging the first front toothing of the groove element;

opposite to the second front toothing, a first radial front toothing provided on an upper surface of the intermediate plate, said first radial front toothing being radial to the centre of the intermediate plate bore and limited by an area having the shape of a segment of a circle;

a supporting member resting on the intermediate plate, the supporting member having a blind bore for receiving the cylindrical peg of the adjustment element, a second radial front toothing arranged on the supporting member such that it is engaged with the first radial front toothing of the plate, and a shaft projecting obliqueradially relative to the blind bore bears a cone for receiving a joint ball;

a joint ball provided with a conical recess corresponding to the cone, the conical recess having an adjustable press-in depth;

a fastening element in contact with an internal thread of the peg through a bore in the supporting member, wherein the fastening element has a tightened condition wherein the fastening element braces the groove element, the intermediate plate, the supporting member, and the engaged locking means against each other; and the plane of the medio-lateral displaceability of the prosthesis head running parallel to a tangent resting on the lateral edge of the proximal femoral infundibulum and contacting the inner contour of the curved neck of the femur.

18. The adjustable prosthesis head according to claim 17, wherein the endoprosthesis has a shaft mounted to the adjustable prosthesis head, and wherein the plane of the medio-lateral displaceability is inclined in a medially ascending manner in the range of about 1 to 15° relative to a line perpendicular to a shaft axis.

* * * * *